(12) United States Patent
Cappello

(10) Patent No.: US 8,334,131 B2
(45) Date of Patent: Dec. 18, 2012

(54) FORMULATIONS FOR PROMOTING STEM CELL NUTRITION

(76) Inventor: John V. Cappello, King of Prussia, PA (US)

( * ) Notice: Subject to any disclaimer, the term of this patent is extended or adjusted under 35 U.S.C. 154(b) by 0 days.

(21) Appl. No.: 13/425,563

(22) Filed: Mar. 21, 2012

(65) Prior Publication Data

US 2012/0251501 A1   Oct. 4, 2012

Related U.S. Application Data

(60) Provisional application No. 61/465,929, filed on Mar. 28, 2011.

(51) Int. Cl.
   *C12N 1/12*   (2006.01)
   *A61K 36/02*  (2006.01)

(52) U.S. Cl. .................. 435/257.1; 424/195.17

(58) Field of Classification Search ........................ None
   See application file for complete search history.

(56) References Cited

U.S. PATENT DOCUMENTS

| | | | |
|---|---|---|---|
| 5,770,215 A * | 6/1998 | Moshyedi | 424/440 |
| 2006/0233737 A1* | 10/2006 | Janailhac et al. | 424/74 |
| 2008/0085330 A1* | 4/2008 | Davis Sanberg et al. | 424/729 |
| 2008/0085344 A1* | 4/2008 | Williams et al. | 426/73 |
| 2008/0138321 A1* | 6/2008 | Jensen et al. | 424/93.4 |
| 2008/0145380 A1* | 6/2008 | Teas | 424/195.17 |
| 2008/0260881 A1* | 10/2008 | Cappello | 424/780 |
| 2009/0311286 A1* | 12/2009 | Scoglio et al. | 424/195.17 |

OTHER PUBLICATIONS http://web.archive.org/web/20081201022519/http://www.bluegreenfoods.com/breakdown.htm—web archived version from Dec. 1, 2008.*

* cited by examiner

*Primary Examiner* — Chris R Tate
*Assistant Examiner* — Douglas F White
(74) *Attorney, Agent, or Firm* — Lawrence J. Shurupoff

(57) ABSTRACT

A a multivitamin and mineral dietary supplement includes a base composition of whole aphanizomenon flos-aqua, phycocyanin and phenylethylamine for promoting the body's natural production of stem cells. The production, support and maintenance of these stem cells is enhanced with vitamins and/or minerals. The vitamins and minerals when combined with the base composition promote good health, body repair and longevity.

8 Claims, No Drawings

FORMULATIONS FOR PROMOTING STEM CELL NUTRITION

CROSS REFERENCE TO RELATED APPLICATIONS

This application claims the benefit and priority of U.S. provisional application No. 61/465,929, entitled "Anti-Aging Formulations" filed Mar. 28, 2011, and which is incorporated herein by reference in its entirety. This application is also related to U.S. application number Ser. No. 13/357,280 entitled "Anti-Aging Formulations," filed Jan. 24, 2012 and which is incorporated herein by reference in its entirety.

BACKGROUND

Many attempts have been made to develop treatments and formulations to extend the human lifespan, to improve health, and to improve the quality of life as one ages. To date, few, if any of these attempts have produced superior results, as few approaches fully recognize the basis or causes of aging and illness. It is important to know the causes of aging and the illnesses associated with aging, because as with treating a disease, one must first understand the problem, so that a precise remedy can be applied.

Some of the current theories of aging and illness may be a result of other older conventional theories. Many of these theories are interlinked, in the same complex way that biological processes of the body and the many factors affecting these processes are interlinked.

Approaching any one or a combination of the following theories with a specialized treatment protocol may address and treat health and aging problems on different levels, and help to slow down and eradicate some of the causes of aging and illness. In order to appreciate the diversity of thought on the causes of aging and illness, some of the current theories are outlined below.

The DNA and Genetic Theories

Some scientists regard the DNA and genetic theories as planned obsolescence theories because they focus on the encoded programming within DNA. DNA is the blueprint of individual life obtained from one's parents. Humans are born with a unique code and a predetermined tendency to certain types of physical and mental functioning that regulate the rate at which one ages.

This type of genetic clock can be greatly influenced with regard to its rate of timing. For example, DNA is easily oxidized and this damage can be accumulated from diet, lifestyle, toxins, pollution, radiation and other outside influences. Thus, each individual has the ability to accelerate DNA damage or slow it down.

One recent theory regarding gene damage is the telomerase theory of aging. A telomere is the repetitive DNA sequence located at the end of a chromosome which shortens progressively with each cell division and limits the replicative potential of normal human somatic cells. It is now understood that telomeres, the sequences of nucleic acids extending from the ends of chromosomes, shorten every time a cell divides. This shortening of telomeres is believed to lead to cellular damage due to the inability of the cell to duplicate itself correctly. Each time a cell divides it duplicates itself a little less accurately or worse than the time before. This eventually leads to cellular dysfunction, physical aging, illness and death.

Further research indicates that telomeres can be repaired by the introduction of a relevant hormone. Telomeres and their subsequent processes affect each other. Once we know what each telomere is responsible for, we may precisely introduce the necessary hormone and aid genetic repair, as well as hormonal balance.

Another key element in rebuilding the disappearing telomeres and improving health is the enzyme telomerase, an enzyme so far only found in germ and cancer cells. Telomerase appears to repair and replace telomeres helping to re-regulate the clock that controls the lifespan of dividing cells.

The Neuroendocrine Theory

This theory of physical aging elaborates on wear and tear by focusing on the neuroendocrine system. This system is a complicated network of biochemicals that govern the release of hormones which are altered by the walnut sized gland, the hypothalamus, located in the brain.

The Free Radical Theory

The term free radical describes any molecule that has a free electron. This property makes the free radical molecule react with healthy molecules in a destructive way. Because the free radical molecule has an extra electron, it creates an extra negative charge. This unbalanced energy makes the free radical bind itself to another balanced molecule. In so doing, the balanced molecule becomes unbalanced and thus a free radical itself. It is known that diet, lifestyle, drugs (e.g. tobacco and alcohol) and radiation are all accelerators of free radical production within the body and can influence the rate of aging.

The Membrane Theory of Aging

According to this theory, it is the age-related changes of the cells' ability to transfer chemicals, heat and electrical processes that impair the integrity of the cells.

As one grows older, cell membranes become less lipid, less watery and more solid. This impedes the cell's ability and efficiency to conduct normal cell functions. In particular, this can lead to a toxic accumulation within the body's cells. This cellular toxin is referred to as lipofuscin and as one grows older lipofuscin deposits become more present in the brain, heart and lungs and also in the skin. Some of the skin age-pigments referred to as liver spots or age spots are composed of lipofuscin. It is known that Alzheimer disease patients have much higher levels of lipofuscin deposits than compared to their healthy control groups. The cells' declining efficiency also means that the essential and regular transfer of sodium and potassium is impaired, thus reducing cellular communication. It is also believed that electrical conduction and heat transfer is also impaired by this cellular degradation.

The Hayflick Limit Theory

The Hayflick Limit Theory of aging suggests that the human cell is limited in the number of times it can divide. Part of this theory may be affected by cell waste accumulation (which is described in the Membrane Theory of aging). It is theorized that the human cell's ability to divide is limited to approximately 50 times, after which it simply stops dividing (and hence dies). It has been shown that nutrition has an effect on cells, with overfed cells dividing much faster than underfed cells. As cells divide to help repair and regenerate themselves the DNA & Genetic Theory of Aging may play a role. Each time a cell divides it may lose some blue-print information. Eventually (after 50-odd times of division) there is simply not enough DNA information available to complete any sort of division.

The Mitochondrial Decline Theory

The mitochondria are the power producing organelles found in every cell of every organ. Their primary job is to create adenosine triphosphate (ATP). They do so in the various energy cycles that involve nutrients such as acetyl-L-carnitine, CoQ10 (idebenone), NADH and some B vitamins. As the mitochondria decline, aging increases.

The Cross-Linking Theory

The Cross-Linking Theory of aging is also referred to as the glycosylation theory of aging. In this theory, it is the binding of glucose (simple sugars) to protein, (a process that occurs under the presence of oxygen) that causes various aging problems. Once this binding has occurred, the protein becomes impaired and is unable to perform as efficiently. Living a longer life leads to the increased possibility of oxygen meeting glucose and binding glucose to protein. This can lead to cross-linking disorders including senile cataracts and the appearance of tough, leathery and yellow skin.

SUMMARY

In accordance with this disclosure, a new approach to promoting health and longevity is to provide a combination of vitamins and minerals to increase both the amount or number of stem cells produced naturally by the body and to further increase the effectiveness or efficiency of stein cells in repairing and renewing the body's cells. While the vitamins and minerals disclosed herein are effective alone in promoting stem cell nutrition and increasing the amount of adult stem cells in the human body, it has been found that by combining such vitamins and mineral with additional stem cell promoting ingredients, a more potent and effective production and differentiation of stem cells can be achieved.

That is, by combining one or more of the vitamins and minerals disclosed herein with one or more of the ingredients disclosed in U.S. Pat. No. 7,473,427, which is incorporated herein by reference in its entirety, the body's natural production of stem cells will be enhanced, and the ability of stem cells to differentiate or convert into different types of tissue cells, i.e., the "plasticity" of these cells, will also be enhanced.

The combination of vitamins and minerals with one or more of blue green algae, phycocyanin and phenylethylamine (PEA) provides more circulating stem cells having the ability to produce more tissue for repairing the body and maintaining and enhancing health. The formulations disclosed below not only provide stem cell nutrition support, but also provide the daily vitamins and minerals required for sustaining health.

Up to 75 micronutrients are provided within blue green algae to improve health and support life. Extra vitamin D3 (above the minimum daily requirement) increases the production of stem cells in bone marrow, resulting in a larger number of stem cells circulating in the blood.

Vitamin C increases the ability of stem cells to differentiate into various types of tissue cells. That is, all circulating stem cells are able to convert or differentiate into tissue cells. With the ingestion of vitamin C, a greater percentage of circulating stem cells are able to differentiate into tissue cells, thereby increasing the efficiency and effectiveness of stem cell differentiation and the resulting repair of body tissue.

Subjects taking the vitamin, mineral and stem cell promoting formulations disclosed below report having more energy, fewer headaches, less joint pain, more stamina, clearer thinking and improved mental clarity and have a general sense of well being and a sense of simply feeling better. These formulations not only support stem cell nutrition but also support the body's immune system.

The formulations discussed below help to rebuild the body's tissues using the body's own natural renewal system based on the body's natural production of adult stem cells. Extra adult stem cells circulate through the body from the body's own bone marrow to improve the body's own repair process. At the same time, the body absorbs the minimum daily requirements of the most commonly needed vitamins and minerals as well as absorbing extra amounts of vitamins selected to enhance stem cell production and stem cell performance.

DESCRIPTION OF REPRESENTATIVE EMBODIMENTS

As noted above, good health and efficient body repair can be promoted with the administration of vitamins and minerals. However, while vitamins and minerals alone can help to promote stem cell production, an improved and beneficial result can be achieved by combining vitamins and/or minerals with a formulation that further promotes stem cell growth and nutrition. One such formulation is disclosed in U.S. Pat. No. 7,473,427 wherein blue green algae provides the essential vitamins, minerals, proteins and nutrients required to support life. One form of blue-green algae known as aphanizomenon flos-aqua (AFA) is particularly effective in stimulating natural stem cell production within the body. Stem cells not only combat disease, they contribute to health maintenance and reduce the effects of injury and aging.

As further described in U.S. Pat. No. 7,473,427, by combining phycocyanin with AFA, inflammation such as caused by injury, arthritis or irritants can be reduced or even prevented. Phycocyanin can be extracted in a concentrated form from AFA and provided as a supplement to AFA. Alternatively, phycocyanin can be provided in the form of arthrospira platentis. While phycocyanin is available in the form of an extract of AFA, phycocyanin can also be provided in the less expensive form of arthrospira platentis ("AP"), which contains about 18% to 20% of phycocyanin. Phenylethylamine (PEA) such as in the form of beta-phenylethylamine hydrochloride, can also be combined with AFA to reduce depression and promote alertness.

The combination of at least about 250 mg of whole blue-green algae, such as AFA, at least about 25 mg of phycocyanin and at least about 0.35 mg of phenylethylamine supports an increased life span and improved quality of life by enhancing the metabolic function and activation of SIRT-1 anti-aging genes. This in turn encourages the production of new cells with longer telomeres. It is believed this combination or blend of ingredients can repair shortened telomeres as well as decrease the rate of telomere shortening in both new and existing cells.

The combination of whole blue-green algae (such as AFA), with phenylethylamine (PEA) and phycocyanin aids in nourishing and increasing the production of adult stem cells in circulation. These newly produced stem cells can replace older cells in the body with newer cells having longer telomeres on their chromosomes. This resists the aging process which has been associated with a decrease in telomere length.

The PEA available naturally in AFA is further enhanced in accordance with this disclosure with supplemental phenylethylamine (PEA) complex resulting in a concomitant well being effect. It is believed that the combination of whole AFA, added phycocyanin extracted from AFA and from enriched AP components plus added. PEA complex taken in increased amounts over those disclosed in U.S. Pat. No. 7,473,427 helps to increase progenitor or adult stem cells naturally and create greater feelings of well being.

Just how much of an increase in stem cells and well being achieved is an individual response, as studies done to date were done with healthy subjects. Results will vary upon each person's current age, health condition and quantity of the subject dietary composition ingested.

The more stem cells or "building blocks" we have available, the faster and better our organs can be repaired. Our overall health is strongly influenced by the continued availability of extra stem cells in our bodies. But as we age our natural stem cell count declines. Natural adult stem cells can migrate to damaged tissues and actually become a new heart cell, liver cell, pancreas cell or any type of tissue cell. They rapidly multiply and can become any kind of cell in a short time.

While the combination of whole blue-green algae, PEA and phycocyanin provides an effective primary or "base composition" for stimulating stem cell production, the ingredients in this base composition can be made more effective in stimulating and nourishing stem cell production with the addition of one or more of the ingredients disclosed below. That is, it has been found that by supplementing this base composition with one or more additional ingredients, the amount of stem cell production, body repair and the degree of anti-aging can be significantly improved. The result is a life-extending dietary supplement that not only retards the aging process but also repairs prior damage to existing cells.

By adding vitamins and/or minerals to the base composition, greater health benefits can be achieved. For example, vitamin D3, noted above, is a potent inhibitor of the inflammatory response and has been associated with increased stem cell circulation. Vitamin D3 can enhance both telomere length and improve adult stem cell circulation. Adding vitamin D3 to the base composition alone or in combination with other vitamins and minerals stimulates the activation of dormant adult stem cells in the bone marrow, leading to improved stem cell production. While the minimum daily requirement (MDR) of 400 IU of vitamin D3 is standard or common, 250 IU to 5000 IU (6.25 mcg. to 125 mcg.) of vitamin D3 and preferably 1000 to 2000 IU (25 mcg. to 50 mcg.) of vitamin D3 can be taken in combination with the base composition, alone or with any one or more of the other ingredients disclosed herein.

Vitamin C can be added to the base composition alone or in combination with one or more of the other ingredients disclosed herein. As noted above, vitamin C increases the differentiating abilities of adult stem cells. Vitamin C can be added to the base composition in the amount of 15 mg to 90 mg or more per dosage.

The base composition can be combined with one or more additional vitamins and/or minerals to further promote health and longevity. Telomere length can be increased by up to 5% by taking a multivitamin and mineral formulation on a daily basis. By combining the base composition of AFA, phycocyanin and PEA in the amounts and ranges as set forth herein and as described in U.S. Pat. No. 7,473,427, one can further increase one's health and longevity significantly.

For example, by adding one or more, all, or any combination of the following vitamins and minerals to the base formulation, a life enhancing result can be achieved over and above that provided by the base composition. In this table, the base composition is listed last in the form of a commercially available product sold under the brand Vita Stim.

| Vitamin/Mineral | Percent of Daily Values | |
|---|---|---|
| | Amount | % of Daily Values |
| Vitamin A (20% as beta carotene) | 5000 IU | 100% |
| Vitamin D3 | 1000 IU | 250% |
| Vitamin C | 90 mg. | 100% |
| Vitamin E | 30 IU | 100% |
| Vitamin K | 40 mcg. | 50% |
| Thiamin (Vitamin B1) | 2.3 mg. | 150% |
| Riboflavin (Vitamin B2) | 2.6 mg. | 150% |
| Niacin | 20 mg. | 100% |
| Folic Acid | 400 mcg. | 100% |
| Vitamin B12 | 9 mcg. | 100% |
| Calcium | 200 mg. | 20% |
| Biotin | 300 mcg. | 100% |
| Pantothenic Acid | 10 mg. | 100% |
| Calcium | 200 mg. | 20% |
| Iron | 6 mg. | 33% |
| Phosphorous | 45 mg. | 4% |
| Iodine | 150 mcg. | 100% |
| Magnesium | 100 mg. | 25% |
| Zinc | 15 mg. | 100% |
| Selenium | 70 mcg. | 100% |
| Copper | 2 mg. | 100% |
| Manganese | 2 mg. | 100% |
| Chromium | 120 mcg. | 100% |
| Molybdenum | 75 mcg. | 100% |
| Emergent Health ™ Vita-Stim Concentrate | 475 mg. | Not Established |

The blend of vitamins and minerals listed above can be advantageously combined with a base composition of 250 mg. of whole AFA, 200 mg. of arthrospira platensis containing 18%-20% of phycocyanin, and 25 mg. of phenylethylamine. The resulting aggregate dietary composition can be provided in the form of two 900 mg pills or tablets to be taken orally at least once a day and potentially twice a day. While the amounts listed above provide effective results, each amount can be reduced by as much as 50% or increased by as much as 200%, 300% or more for even more effective results.

It should be noted that one commercially available source of the base composition is a product currently distributed by Emergent Health Corporation (www.emergenthealth.com) of King of Prussia, Pa. under the brand "Vita-Stim." Combining one or more Vita-Stim capsules with daily vitamins and minerals including any, all or a subset of the vitamins and minerals listed above not only improves health but increases the quality of life and promotes longevity. Each 900 mg pill or tablet noted above contains about 125 mg of whole AFA, 100 mg of AP containing 18% to 20% of phycocyanin and 12.5 mg of PEA providing in two 900 mg pills or tablets 250 mg of whole AFA, 200 mg of AP containing 18%-20% phycocyanin and 25 mg of PEA.

The vitamin and mineral formulation set forth in the table above, when added to the base composition, provides a daily vitamin and mineral formulation with complete stem cell nutrition support. The combination of whole (AFA) and two distinct components that can be extracted from AFA, namely phycocyanin (also found in arthrospira platensis (AP)) and phenylethylamine (PEA) complex increases adult stem cell production naturally from bone marrow. The amount of the base composition that can be combined with the vitamins and minerals listed above are 250 mg. of whole AFA, 200 mg. of arthrospira platensis containing 18%-20% phycocyanin (or about 40 mg. of phycocyanin) and 25 mg. of PEA such as beta phenylethylene hydrochloride pharmaceutical grade USP. This 475 mg. blend of the base composition can be taken orally in the form of two Vita-Stim capsules noted above. It is possible to reduce this dosage in half by taking only one Vita-Stim capsule or increase this dosage to three or four Vita-Stim capsules in combination with one or more vitamins and/or one or more minerals as noted above.

One study has shown an increase of up to 2,500,000 new adult stem cells in blood circulation based on unidentified AFA biochemical components. One component of AFA in particular (phycocyanin) has been shown to demonstrate the capacity, along with added polysaccharide, to influence the differentiation and proliferation of committed hematopoietic progenitor cells from the bone marrow.

Another benefit of the base composition is the added nutritional content it can add to one's life. The base composition contains, when provided in commercial form as a Vita-Stim capsule noted above:

Protein 60-75%
Carbohydrates 20-30%
Lipids 2-8%
Minerals 3-9%
Pigments 1-4%
Moisture 0-7%
Chlorophyll A 4-2%

On a per gram basis, Vita-Stim base formulation concentrate can also provide up to all of the following:

Vitamins:
Provitamin A Beta Carotene 2000 IU, Vitamin E 1.70 IU, Thiamin (B1) 4.70 mcg., Ascorbic Acid (Vitamin C) 6.70 mg., Riboflavin (B2) 57.30 mcg., Biotin 0.30 mcg., Niacin (B3) .16 mg., Folic Acid 1.00 mcg., Pantothenic Acid (B5) 6.80 mcg., Choline 2.30 mcg., Pyridoxine (B6) 11.10 mcg., Cobalamin (B12) 8.00 mcg., Inositol 160 mcg., Vitamin K 45.52 mcg.

Minerals:
Boron 0.15 mg., Iodine 0.53 mcg., Selenium 0.67 mcg., Calcium 14.00 mg., Iron 350.70 mcg., Silicon 186.50 mcg., Chloride 0.47 mg., Magnesium 2.20 mg., Sodium 2.70 mg., Chromium 0.53 mcg., Manganese 32.00 mcg., Tin 0.47 mcg., Cobalt 2.00 mcg., Molybdenum 3.30 mcg., Titanium 46.60 mcg., Copper 4.30 mcg., Nickel 5.30 mcg., Vanadium 2.70 mcg., Fluoride 38.00 mcg., Potassium 12.00 mcg., Zinc 18.70 mcg., Germanium 0.27 mcg., Phosphorus 5.20 mcg.

Typical Amino Acid Content (Per Gram)
Essential Amino Acids
Arginine 38 mg., Methionine 7 mg., Histidine 9 mg., Phenylalanine 25 mg., Isoleucine 29 mg., Threonine 33 mg., Leucine 52 mg., Tryptophan 7 mg., Lysine 35 mg., Valine 32 mg.

Non-essential Amino Acids:
Alanine 47 mg., Glutamine 78 mg., Asparagine 47 mg., Glycine 29 mg., Aspartic Acid 7 mg., Proline 29 mg., Cystine 2 mg., Serine 29 mg., Glutamic Acid 4 mg., Tyrosine 17 mg.

There has been disclosed heretofore the best embodiments presently contemplated. However, it is to be understood that various changes and modifications may be made thereto without departing from the spirit of the disclosure.

What is claimed is:

1. A dietary composition for promoting stem cell production and stem cell differentiation within a human body comprising:
   at least about 250 mg of blue green algae;
   at least about 25 mg of phycocyanin;
   at least about 0.35 mg of phenylethylamine;
   from about 6.25 mg to 125 mg of Vitamin D3 for improving stem cell circulation within the human body; and
   at least about 15 mg of Vitamin C for increasing the ability of stem cells to differentiate within the human body.

2. The composition of claim 1, wherein said phycocyanin is provided as a component of *Arthrospira platensis*.

3. The composition of claim 1, further comprising one or more supplemental vitamins selected from the group consisting of vitamin A, vitamin C, vitamin E, vitamin K, thiamin, riboflavin, niacin, vitamin B6, folic acid, vitamin B12, biotin and pantothenic acid.

4. The composition of claim 1, wherein said blue green algae comprises *Aphanizomenon flos-aqua*.

5. The composition of claim 1, further comprising one or more supplemental minerals selected from the group consisting of calcium, iron, phosphorus, iodine, magnesium, zinc, selenium, copper, manganese, chromium and molybdenum.

6. The composition of claim 1, further comprising boron, iodine, selenium, calcium, iron, silicon, chloride, magnesium, sodium, chromium, manganese, tin, cobalt, molybdenum, titanium, copper, nickel, vanadium, fluoride, potassium, zinc, germanium, and phosphorus.

7. The composition of claim 1, wherein said vitamin D3 comprises at least 1000 IU of vitamin D3.

8. The composition of claim 1, wherein said vitamin C comprises at least 90 mg. of vitamin C.

* * * * *